United States Patent
Durrani

(10) Patent No.: US 11,039,995 B2
(45) Date of Patent: Jun. 22, 2021

(54) TOPICAL COMPOSITIONS FOR REDUCING THE EFFECTS OF AGING

(71) Applicant: Samson Pharma, LLC, Scottsdale, AZ (US)

(72) Inventor: Manzer J. Durrani, Phoenix, AZ (US)

(73) Assignee: SAMSON PHARMA, LLC, Scottsdale, AZ (US)

( * ) Notice: Subject to any disclaimer, the term of this patent is extended or adjusted under 35 U.S.C. 154(b) by 109 days.

(21) Appl. No.: 16/380,808

(22) Filed: Apr. 10, 2019

(65) Prior Publication Data

US 2019/0298629 A1 Oct. 3, 2019

Related U.S. Application Data

(63) Continuation of application No. 14/775,920, filed as application No. PCT/US2014/030033 on Mar. 15, 2014, now abandoned.

(60) Provisional application No. 61/789,701, filed on Mar. 15, 2013, provisional application No. 61/790,370, filed on Mar. 15, 2013.

(51) Int. Cl.
| | |
|---|---|
| *A61K 36/16* | (2006.01) |
| *A61K 8/42* | (2006.01) |
| *A61K 8/365* | (2006.01) |
| *A61K 8/81* | (2006.01) |
| *A61K 8/86* | (2006.01) |
| *A61Q 19/08* | (2006.01) |
| *A61K 8/9771* | (2017.01) |
| *A61K 8/06* | (2006.01) |
| *A61K 8/19* | (2006.01) |
| *A61K 8/34* | (2006.01) |
| *A61K 8/37* | (2006.01) |

(52) U.S. Cl.
CPC ........... *A61K 8/42* (2013.01); *A61K 8/062* (2013.01); *A61K 8/19* (2013.01); *A61K 8/34* (2013.01); *A61K 8/347* (2013.01); *A61K 8/365* (2013.01); *A61K 8/37* (2013.01); *A61K 8/8152* (2013.01); *A61K 8/86* (2013.01); *A61K 8/9771* (2017.08); *A61Q 19/08* (2013.01); *A61K 2800/49* (2013.01); *A61K 2800/52* (2013.01); *A61K 2800/522* (2013.01); *A61K 2800/596* (2013.01); *A61K 2800/75* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 5,556,844 A | 9/1996 | Reichert et al. | |
| 5,624,957 A | 4/1997 | Swann et al. | |
| 6,080,393 A | 6/2000 | Liu et al. | |
| 6,551,605 B2 * | 4/2003 | Bonda | A61K 8/37 424/401 |
| 7,126,017 B2 | 10/2006 | DeLuca et al. | |
| 7,314,639 B2 | 1/2008 | Kagechika et al. | |
| 7,750,043 B2 | 7/2010 | Deluca et al. | |
| 8,030,360 B2 | 10/2011 | Shudo et al. | |
| 8,252,837 B2 | 8/2012 | Ekimoto | |
| 9,845,508 B2 | 12/2017 | Chen et al. | |
| 9,868,994 B2 | 1/2018 | McKeown et al. | |
| 10,668,039 B2 | 6/2020 | Zon et al. | |
| 10,697,025 B2 | 6/2020 | Chen et al. | |
| 2002/0022040 A1 * | 2/2002 | Robinson | A61K 31/455 424/401 |
| 2002/0197285 A1 | 12/2002 | Bonda | |
| 2005/0202055 A1 | 9/2005 | Shudo et al. | |
| 2008/0139842 A1 | 6/2008 | Shudo et al. | |
| 2008/0255069 A1 | 10/2008 | Shudo et al. | |
| 2008/0261925 A1 | 10/2008 | Clagett-Dame et al. | |
| 2009/0253796 A1 | 10/2009 | Ryozo et al. | |
| 2009/0281184 A1 | 11/2009 | Norimasa et al. | |
| 2010/0048708 A1 * | 2/2010 | Ekimoto | A61K 47/10 514/563 |
| 2015/0164836 A1 | 6/2015 | Wu | |
| 2016/0000674 A1 | 1/2016 | Durrani | |
| 2017/0079942 A1 | 3/2017 | Akira et al. | |
| 2017/0281559 A1 | 10/2017 | Chaudhary | |
| 2018/0333380 A1 | 11/2018 | Ghiaur et al. | |
| 2019/0134152 A1 | 5/2019 | Durham | |
| 2019/0298629 A1 | 10/2019 | Durrani | |
| 2020/0061007 A1 | 2/2020 | Kurisaki et al. | |

FOREIGN PATENT DOCUMENTS

| | | |
|---|---|---|
| CN | 1897930 | 1/2007 |
| CN | 102961346 A1 | 3/2013 |
| JP | 8-193019 | 7/1996 |
| JP | 2016-518342 | 6/2016 |
| JP | 6-501458 | 3/2019 |
| WO | 96/30009 | 10/1996 |
| WO | 2005/087220 | 9/2005 |
| WO | 2008/120711 | 10/2008 |

(Continued)

OTHER PUBLICATIONS

Paudel, Kalpana S. et al.; Challenges and opportunities in dermal/transdermal delivery; Ther Deliv. 1(1): 109-131; Jul. 2010.
Brittain, Harry G., PhD.; Thermodynamic vs. Kinetic Solubility: Knowing Which is Which; American Pharmaceutical Review; Apr. 29; 2014; URL: https://www.americanpharmaceuticalreview.com/Featured-Articles/1604552-Thermodynamic-vs-Kinetic-Solubility-Knowing-Which-is-Which/.
Nixon, G.A. et al.; Interspecies comparisons of skin irritancy; Toxicology and Applied Pharmacology; vol. 31; Issue 3, pp. 481-490; Mar. 1975.
Pople et al. (2006) AAPS PharmSciTech 7(4): Article 91 E1-E7.
Tegeli et al. Pemulen as a versatile emulsifier; International Journal of Drug Formulation & Research; vol. 2(1): 52-63 (2011).

(Continued)

*Primary Examiner* — Russell G Fiebig
(74) *Attorney, Agent, or Firm* — Bass, Berry & Sims, PLC

(57) ABSTRACT

The present invention comprises ternary compositions of tamibarotene and/or ammonium lactate in Pemulen for treatment of effects of aging.

17 Claims, No Drawings

(56) References Cited

FOREIGN PATENT DOCUMENTS

| WO | 2009/151914 | 12/2009 |
|---|---|---|
| WO | 2014/145295 A1 | 9/2014 |
| WO | 2019/044670 A1 | 3/2019 |
| WO | 2019086723 A1 | 5/2019 |
| WO | 2019/160806 A2 | 8/2019 |

OTHER PUBLICATIONS

Müller-Goymann C. Pharm Res. Liquid Crystals in Emulsions, Creams, arid Gels Containing Ethoxylated Sterols as Surfactant Jul. 1984;1(4):154-8. doi: 10.1023/A:1016392407150.

Hammouda et al.; SANS from dPS/PVME/hPS ternary polymer blends, Polymer 33:8, pp. 1785-1787 (1992).

Kim, Hyunjo, et al.; A New Ternary Polymeric Matrix System for Controlled Drug Delivery of Highly Soluble Drugs : 1. Diltiazern Hydrochloride, Pharmaceutical Research; 14,(10), 1415-1421 (1997).

Bitchikh, Karima; et al. Modeling of Ternary Solid-Liquid-Equilibria for Pharmaceutical and Food Systems, Chemical Engineeringtransactions vol. 43, pp. 1873-1878, (2015).

Hamedi M., Construction of solid-liquid phase diagrams in ternary systems by titration calorimetry; Thermochimica Acta, 44, 70-74, 2006.

Reid B. et al.; PEG hydrogel degradation and the role of the surrounding tissue environment; J Tissue Eng Regen Med. Mar. 2013; 9(3):315-318. doi: 10.1002/term.1688. Epub Mar. 12, 2013.

* cited by examiner

TOPICAL COMPOSITIONS FOR REDUCING THE EFFECTS OF AGING

CROSS REFERENCE TO RELATED APPLICATION

This application is a U.S. National Stage patent application under 35 U.S.C. § 371 of International Patent Application No. PCT/US2014/030033, filed on Mar. 15, 2014, which claims priority to U.S. Provisional Patent Application No. 61/790,370, filed on Mar. 15, 2013, and to U.S. Provisional Patent Application No. 61/789,701, filed on Mar. 15, 2013, the contents of which are expressly incorporated by reference. All references cited herein are expressly incorporated by reference in their entirety.

BACKGROUND OF THE INVENTION

The present invention relates to novel cosmetic, and pharmaceutical compositions containing tamibarotene or ammonium lactate for topical application in the treatment of wrinkles and dry skin.

Cosmetic preparations are widely used to improve looks or the way a person feels about themselves. To be successful products must deliver visible results without side effects and should appear natural. Various retinoids are known for their antiaging properties Tamibarotene is a new synthetic retinoid drug recently approved for relapsed or refractory acute promyelocytic leukemia (APL) in Japan. It is a specific agonist for retinoic acid receptor alpha/beta.

in clinical trials. Miwako I, Kagechika H R&R Inc., Tokyo, Japan. Drugs of Today (Barcelona, Spain: 1998) [2007, 43(8):563-568]. The structure of tamibarotene is shown below.

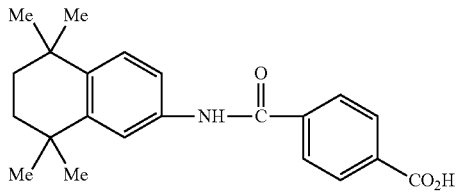 [SMILES: CC1(C)CCC(C)(C)c2cc(NC(=O)c3ccc(C(=O)O)cc3)ccc21]

Tamibarotene

CAS No.: 94497-51-5

Name: Benzoic acid,4-[[(5,6,7,8-tetrahydro-5,5,8,8-tetramethyl-2-naphthalenyl)amino]carbonyl]—

Superlist Name: Tamibarotene

Formula: C22H125NO3

Synonyms: 4-[(5,6,7,8-Tetrahydro-5,5,8,8-tetramethyl-2-naphthalenyl)carbamoyl]benzoicacid;N-(5,6,7,8-Tetrahydro-5,5,8,8-tetramethyl)-2-naphthyl)terephthalamic acid; Am 80 (pharmaceutical);Amnolake;NSC 608000;Retinoid AM 80;

Molecular Weight: 351.44

Tamibarotene may be synthesized as follows:

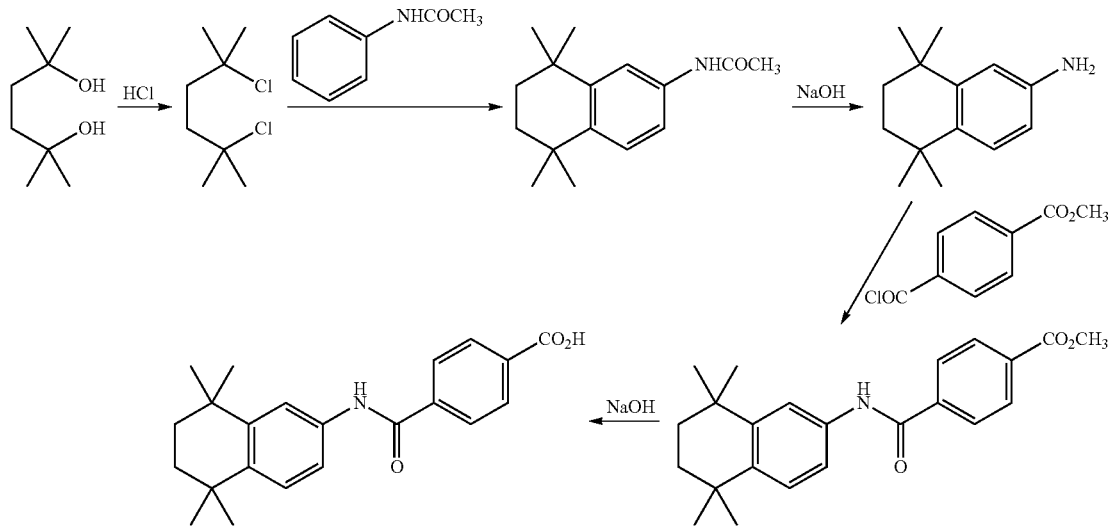

Tamibarotene is orally active and was developed to overcome all-trans retinoic acid (ATRA) resistance, with potential antineoplastic activity.

Compared to all-trans retinoic acid (ATRA), a natural retinoid indicated for a first-line treatment of APL, tamibarotene is chemically more stable and several times more potent as an inducer of differentiation in promyelocytic leukemia cells. In contrast to ATRA, whose plasma concentration declines considerably during daily administration, tamibarotene sustains plasma level probably due to a lower affinity for cellular retinoic acid binding protein. Furthermore, adverse side effects were milder than those of ATRA Formulation of cosmetics is well known in the art, United States published patent publication number 20110059892 to Phillippe Moussou provides examples of excipients widely use in cosmetic products.

Formulation of retinoids for topical delivery is problematic in that the formulations are unstable and rapidly degrade.

Ammonium lactate is a moisturizing agent known in the art that is typically formulated as an oil in water emulsion for topical administration. Currently available products suffer from the problem that sufactants used to emulsify sunscreen agents also remove the agents used to promote absorption from the skin when in the presence of water. This causes loss of UV absorbent activity and sun protectant effects sunscreen agents is lost.

The present ammonium lactate formulation solves the problem by using a new emulsification technology based on Pemulen. This invention provides novel cosmetic combination compositions of ammonium lactate http://www.drugs.com/ingredient/ammonium, in a novel polymeric emulsification technology using Acrylates/C10-30 Alkyl Acrylate Crosspolymer, (Pemulen™ TR-1 Polymeric Emulsifier). The Acrylates/C10-30 Alkyl Acrylate Crosspolymer, is a versatile polymer which can emulsify up to 30% oil by weight, within a pH range of 4-5.5, and up to 20%, oil over the pH range of 3-11. Oil-in-water creams typically at 0.1 percent methyl and propyl parabens are used at levels ranging from 0.01 to 0.3% and fragrance in an ternary sterically stabilized emulsion for topical improvement of skin appearance in normal and aged human skin. Like other oil in water cosmetic emulsions, creams have traditionally been emulsified with stearate or nonionic surfactants at 2%-6%. Inherent to surfactant emulsification of UV absorbers is the propensity for the surfactants to remove the absorbers from the skin when contacted

DESCRIPTION OF THE INVENTION

Tamibarotene Compositions

This invention provides novel topical cosmeceutical combinations of compositions of tamibarotene, a natural and synthetic phytochemical and salts with ammonium lactate, bisabalol, polyvinyl pyrrolidone (PVP K15 to K90) for improvement of skin appearance in normal and aged human skin.

The present formulations are stable for tamibarotene and the formulation itself.

In one embodiment the tamibarotne is dissolved in a polyethylene glycol (PEG) such as PEG 300 which is liquid at room temperature.

In another embodiment the formulation comprises a compositions which is waxy at room temperature such as polyethylene glycol 1,540.

In some embodiments the formulation also contains light mineral oil, glyceryl stearate, PEG-100 stearate, propylene glycol, polyoxyl 40 stearate, glycerin, magnesium aluminum silicate, laureth-4, cetyl alcohol, methyl and propyl parabens, methylcellulose, fragrance and water.

In other embodiments tamibarotene is formulated with 0.05-15 percent lactic acid neutralized with ammonium hydroxide, as ammonium lactate to provide a lotion pH of 4.0-6.0 suitable for use on the skin.

In another embodiment the formulation further comprises an anti-irritant such as bisabalol.

In another embodiment, sunscreens may be part of the formulation.

In yet another embodiment the formulation comprises antioxidants such as butylated hydroxytoluene ("BHT") or vitamin E. BHT in higher concentrations may convey antiviral properties to the formulations herein.

Tamibarotene and salts thereof, can be combined in binary and ternary composition with other phytochemical cosmetic anti-aging agents such as *Rosmarinus officinalis*, specifically carnosic acid, *Vitis vinifera* (grape seed extract), specifically *V. vinifera* contains many phenolic compounds. Anthocyanins can be found in the skin of the berries, hydroxycinnamic acids in the pulp and condensed tannins of the proanthocyanidins type in the seeds. Stilbenoids can be found in the skin and in wood.

It can also be formulated with Citronellol, limonene, fruit acids, *Oenothera biennis* (evening primrose oil, which is used for skin disorders such as eczema, psoriasis, and acne).

*Glycyrrhiza glabra* (licorice extract), *Aframomum angustifolium* seed extract, Diosgenin (wild yam), N6 furfuryladenine (kinetin), and Ergothioneine. These treatments are particularly effective on persons afflicted by stress induced lines and wrinkles and reduction of acne lesions and to improve skin texture and skin color without an increase in puffiness Application of tamibarotene (0.05 to 15 percent) alone or in a composition containing bisabalol, an anti-irritant on a daily basis is effective to reduce deep wrinkles.

Example 1: Tamibarotene Gel

Method of Preparation
1. Calculate the required quantity of 0.05-15 percent of Tamibarotene (Molecular weight ~450), and then calculate each ingredient for the total amount to be prepared 500 g.
2. Accurately weigh/measure each ingredient.
3. Dissolve the Tamibarotene and the butylated hydroxytoluene (BHT) in the polyethylene glycol 300.
4. Melt polyethylene glycol 1,540 at about 55° C.
5. Add the Tamibarotene and BHT solution to the melted base, mix well and allow to cool.
6. Package and label.

Example 2: Methods of Use

Application of tamibarotene (0.05 to 15 percent) formulated as in Example 1 topically to the skin enhances the skin image and reduce the wrinkles for a period from about 8 to about 14 hours.

One of skill in the art will appreciate that considerable deviation from the teachings herein are permissible without departing from the spirit of the invention.

Example 3: Ternary Anti-Wrinkle Emulsion of Tamibarotene

Currently available cosmetic products suffer from the problem that sufactants used to emulsify sunscreen agents also remove the agents used to promote absorption from the skin when in the presence of water. This causes loss of UV absorbent activity and sun protectant effects sunscreen agents is lost.

An embodiment of the present invention solves the problem by using a new emulsification technology based on Pemulen. This invention provides novel cosmetic combination compositions of ammonium lactate http://www.drugs.com/ingredient/ammonium-(1), in a novel polymeric emulsification technology using Acrylates/C10-30 Alkyl Acrylate Crosspolymer, (Pemulen™ TR-1 Polymeric Emulsifier). The Acrylates/C10-30 Alkyl Acrylate Crosspolymer, is a versatile polymer which can emulsify up to 30% oil by weight, within a pH range of 4-5.5, and up to 20% oil over the pH range of 3-11. Oil-in-water creams typically at 0.1 percent methyl and propyl parabens are used at levels ranging from 0.01 to 0.3% and fragrance in an ternary sterically stabilized emulsion for topical improvement of skin appearance in normal and aged human skin. Like other oil in water cosmetic emulsions, creams have traditionally been emulsified with stearate or nonionic surfactants at 2%-6%. Inherent to surfactant emulsification of UV absorbers is the propensity for the surfactants to remove the absorbers from the skin when contacted by water.

Pemulen TR1 is a polymeric emulsifier produced by Noveon. A block copolymer consisting of a poly acrylic acid similar to the Carbopol resins presently used to make aqueous and solvent gels in art conservation (Carbopol 934, Carbopol 940, Carbopol 941) cross-linked with a long-chained methacrylate, this carbomer has a lipohilic regions (the methacrylate) as well as hydrophilic regions (the acrylic acid). In the cosmetic industry literature, Pemulen TR-1 is part of a class of copolymers are referred to as acrylate/C10-30 alkyl acrylate cross polymers (6), having the following structure: See http://pemulentr2.pbworks.com/f/PemulenTR2.pdf These regions of differing affinity allow Pemulen TR1 or TR2 to act as a primary emulsifier, that is, it can be used to make oil in water emulsions without the usual required addition of soap or surfactant.

Pemulen TR1 or TR2 does not form emulsions in the same way that traditional surfactants do. To produce oil in water emulsion, a traditional surfactant surrounds a droplet of oil to keep it suspended in oil. Nonionic surfactants used for cleaning painted surfaces, as described in Wolvers' Cleaning Painted Surfaces: Aqueous Methods, might be used in concentrations as high as 30% to form a macroemulsion.

In contrast, Pemulen TR1 is said to form stable O/W emulsions with as little as 0.4%, binding to the oil droplets with the lipophilic portions of the polymer chain that forms the gel.

Gels made with Pemulen TR-1 are most viscous in the pH range of 5-9. A range of alkaline materials are suggested by the manufacturer to formulate aqueous gels using Pemulen TR-1, including sodium hydroxide, ammonium hydroxide, triethanolamine (TEA), and Ethameen C-25.

One interesting feature possessed by Pemulen is that this emulsifying agent is designed to break when the gel is in contact with a salt concentration similar to what one would find on human skin. This is a desirable in the cosmetics industry where moisturizers need to be quickly delivered and absorbed into the user's skin, but this may be a less desirable characteristic of an emulsion designed to clean works of art. In practice, this breakage of the emulsion has been observed when attempting to clean very grimy areas and allowing the gel to dwell for an extended period. Although the vast majority of cream or emulsion products in the marketplace contain water-insoluble actives, the surfactants can re-emulsify the actives and cause wash-off, leaving the skin unprotected.

Those familiar with the art have countered this phenomenon by incorporating waxes or water resistant, film-forming polymers into their formulations. Such a polymer forms an effective barrier, which prevents absorber wash-off, but it may produce negative aesthetic effects such as long rub-in times and a tacky or heavy feel on the skin. However, a novel combination of tamibarotene and Pemulen® polymeric emulsifiers meet the FDA definition of "water-proof" without the use of film-forming polymers, waxes and the like. Because these emulsions contain very little or no surfactants, the water-insoluble UV absorbers remain on the skin, even after an 80 minute exposure to water. The triggered release of the oil phase upon product application ensures that the absorbers are free to spread onto the epidermis where they are immediately active.

This invention specially formulates tamibarotene to provide a cream pH of 4.5-6.5. It may also contain glycerin, isopropyl palmitate, dimethicone. *ginko biloba*, methyl paraben, propyl paraben or butyl parabens fragrance and water.

In one embodiment Tamibarotene is present from about 0.05-15 percent. Optionally, the formulation comprises alpha-Bisabolol, an anti-irritant, and/or a retinoid, such as Tamibarotene, or a triterpenoid such as Betulen [473-98-3] C30H50O2, molecular mass 442.7 and related compounds like betulin, lupeol, and betulinic acid.

The formula is a ternary formulation consisting of three parts which are ultimately combined to form a stable oil in water emulsion. The order of addition of the ingredients should be followed strictly as written. Otherwise, the ingredients fall out of solution.

TABLE 2

| Ingredient | Percent | Weight (g) |
|---|---|---|
| Ternary Ingredient-Part 1 Order of Addition | | |
| Demineralized Water | 63.1 | 155.5 |
| Methyl Paraben | 0.1 | 0.5 |
| Propyl Paraben | 0.1 | 0.5 |
| Glycerin | 2.0 | 10.0 |
| Tamibarotene (20 wt. %) | 8.0 | 200.0 |
| Total | 73.3 | 366.5 |
| Ternary Ingredient-Part 2 Order of Addition | | |
| Demineralized Water | 18.0 | 90.0 |
| Isopropyl Palmitate | 2.5 | 12.5 |
| Dimethicone (Mw 30,000) | 2.5 | 12.5 |
| White Petrolatum | 1.0 | 5.0 |
| *Ginkgo* (*Ginkgo biloba*) | 1.0 | 5.0 |
| Total | 25.0 | 125.0 |
| Ternary Ingredients-Part 3 Order of Addition | | |
| Pemulen ® TR | 1.5 | 7.5 |
| Fragrance (Belle Air #7564) | 0.2 | 1.0 |
| Total | 1.7 | 8.5 |
| Total all 3 parts | 100.0 | 500.0 |

A. Part 1.

Part 1 is formed as follows:
 a. Add Demineralized water to a 1000 ml beaker. Stirring or Agitation at 600 rpm
 b. Add methyl paraben
 c. Add propyl paraben
 d. Add glycerin
 e. Add Tamibarotene
 f. Increase stirring rate or agitation to 1500 rpm B. Part 2

Part 2 is formed as follows:
 a. Add demineralized water to an 800 ml beaker. Stir or Agitation at 600 rpm
 b. Add Isopropyl palmitate
 c. Add dimethicone
 d. Add white petrolatum
 e. Add *gingko biloba*
 f. Increase agitation or stirring 1500 rpm
 Mix part 1 and part 2 for 30 minutes
 a. Slow agitation or stirring down on part 1 to 600 rpm and blend part 2 into part 1
 b. Increase agitation of the combined formulation to 1,800 rpm for 30 minutes.

C. Part 3

The final formulation is produced as follows:
 a. Slow agitation of combined formulation to 600 rpm
 b. Add Pemulen® TR1 OR TR2 very slowly (all of it)
 c. Increase stirring speed to 1,800 rpm for 30 minutes to disperse all of Pemulen® TR1 OR TR2 d. Increase agitation to 2,800 rpm and hold until the emulsion is smooth and creamy without any of the oils floating on the surface.

e. Slow agitation down to 600 rpm and add the fragrance f. Mix well and place in a proper container (jar or tubes).

Example 4 Tamibarotene Cream

A tamibarotene cream was prepared by conventional methods according to the following formulation (data in % by weight) in Table 3.

TABLE 3

| Phase | Ingredients | INCI name | % by weight |
|---|---|---|---|
| A | Water | Aqua | 67.10 |
|  | Glycerol | Glycerin | 5.00 |
|  | Preservatives |  | q.s. |
| B | Crodafos CES | Cetearyl Alcohol (and) Dicetyl Phosphate (and) Ceteth-10 Phosphate | 5.00 |
|  | Myritol 331 | Coco Glyceride | 6.00 |
|  | Tegosoft TN | C12-15 Alkyl Benzoate | 3.00 |
|  | Tegosoft DC | Decyl Cocoate | 3.00 |
|  | Fitoderme | Squalane | 2.00 |
| C | NaOH solution | Sodium Hydroxide | q.s. |
| D | Dow Corning 345 | Cyclomethicone | 3.00 |
|  | Aristoflex AVC | Ammonium Acryloyldimethyltaurate/ VP Copolymer | 0.40 |
| E | EDG Plus | Ethoxydiglycol | 5.00 |
|  | Tamibarotene# |  | 0.50 |

Adjustments can be made for concentrations

Heat phases A and B separately to 75° C., add phase B to phase A, with stirring, and homogenize, adjust the pH to approx. 5.5-6.5 with phase C, successively add the components of phase D at approx. 65° C. and homogenize. Successively add the components of phase E at approx. 35° C., cool to room temperature and, if necessary, readjust the pH to 5.0-5.5.

Example 5: Testing of Tamibarotene

A study was conducted based upon the following references: OECD 404, Organization for Economic Co-Operation and Development (OECD), Guidelines for the Testing of Chemicals, "Acute Dermal Irritation/Corrosion", adopted 24 Apr. 2002. ISO 10993-12, 2012, Biological Evaluation of Medical Devices—Part 12: Sample Preparation and Reference Materials. ISO/IEC 17025, 2005. General Requirements for the Competence of Testing and Calibration Laboratories.

The skin of three albino rabbits was prepared for testing by clipping the skin of the trunk free of hair at the application sites within 24 hours of the test. The sites of application were not abraded deliberately or accidentally during preparation. Tamibarotene was administered at dose levels of 0.02%, 0.04%, and 0.08% in 60% DMSO. The animals were treated by introducing each dose level (0.5 ml) under gauze patches at individual application sites. The control (0.5 ml of 60% DMSO) was applied to a fourth site.

As it was suspected that tamibarotene might produce severe irritancy/corrosion, a single animal test was initially employed. Test patches of each dose level and control were applied. After three minutes, the skin sites were examined by gently lifting the bandage to examine the skin without bandage removal. Since no serious skin reaction was observed, the sites were examined in the same manner after one hour. The observation at this stage indicated that exposure could humanely be allowed to extend to four hours. If a corrosion effect was observed after three minutes or one hour, the test was to be immediately terminated.

Because an irritation or corrosive effect was not observed in the initial test after one hour, the response was confirmed using two additional animals dosed with each dose level and control at individual application sites for four hours. At the end of the exposure period, the wrapping was removed from and the skin washed with USP sterile Water for Injection (SWFI) to remove any test substance still remaining. The three animals were observed for signs of erythema and edema at 60 minutes, and then at 24, 48, and 72 hours after bandage removal. Observations were scored according to the Draize Scale for Scoring Skin Reactions.

All animals gained weight. None of the test sites presented any signs of erythema or edema at any of the observation points. None of the control sites of any animal at any of the observation periods showed signs of erythema or edema.

The test article was tested for its potential to produce primary dermal irritation after a single topical 4-hour application to the skin of albino rabbits. The test article was considered a non-irritant when tested at dose levels of 0.02%, 0.04%, and 0.08% in 60% DMSO.

Ammonium Lactate Compositions

Ammonium lactate is a moisturizing agent known in the art that is typically formulated as an oil in water emulsion for topical administration. Currently available products suffer from the problem that sufactants used to emulsify sunscreen agents also remove the agents used to promote absorption from the skin when in the presence of water. This causes loss of UV absorbent activity and sun protectant effects sunscreen agents is lost.

The present invention solves the problem by using a new emulsification technology based on Pemulen. This invention provides novel cosmetic combination compositions of ammonium lactate http://www.drugs.com/ingredient/ammonium-(1), in a novel polymeric emulsification technology using Acrylates/C10-30 Alkyl Acrylate Crosspolymer, (Pemulen™ TR-1 Polymeric Emulsifier). The Acrylates/C10-30 Alkyl Acrylate Crosspolymer, is a versatile polymer which can emulsify up to 30% oil by weight, within a pH range of 4-5.5, and up to 20% oil over the pH range of 3-11. Oil-in-water creams typically at 0.1 percent methyl and propyl parabens are used at levels ranging from 0.01 to 0.3% and fragrance in an ternary sterically stabilized emulsion for topical improvement of skin appearance in normal and aged human skin. Like other oil in water cosmetic emulsions, creams have traditionally been emulsified with stearate or nonionic surfactants at 2%-6%. Inherent to surfactant emulsification of UV absorbers is the propensity for the surfactants to remove the absorbers from the skin when contacted by water.

Pemulen TR1 is a polymeric emulsifier produced by Noveon. A block copolymer consisting of a poly acrylic acid similar to the Carbopol resins presently used to make aqueous and solvent gels in art conservation (Carbopol 934, Carbopol 940, Carbopol 941) cross-linked with a long-chained methacrylate, this carbomer has a lipohilic regions (the methacrylate) as well as hydrophilic regions (the acrylic acid). In the cosmetic industry literature, Pemulen TR-1 is part of a class of copolymers are referred to as acrylate/C10-30 alkyl acrylate cross polymers (6), having the following structure:

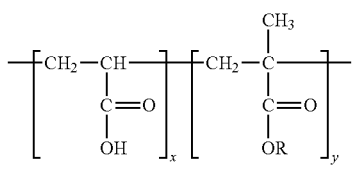

R = long chain alkyl group

See http://pemulentr2.pbworks.com/f/PemulenTR2.pdf

These regions of differing affinity allow Pemulen TR1 or TR2 to act as a primary emulsifier, that is, it can be used to make oil in water emulsions without the usual required addition of soap or surfactant.

Pemulen TR1 or TR2 does not form emulsions in the same way that traditional surfactants do. To produce oil in water emulsion, a traditional surfactant surrounds a droplet of oil to keep it suspended in oil. Nonionic surfactants used for cleaning painted surfaces, as described in Wolvers' Cleaning Painted Surfaces: Aqueous Methods, might be used in concentrations as high as 30% to form a macroemulsion In contrast, Pemulen TR1 is said to form stable O/W emulsions with as little as 0.4%, binding to the oil droplets with the lipophilic portions of the polymer chain that forms the gel.

Gels made with Pemulen TR-1 are most viscous in the pH range of 5-9. A range of alkaline materials are suggested by the manufacturer to formulate aqueous gels using Pemulen TR-1, including sodium hydroxide, ammonium hydroxide, triethanolamine (TEA), and Ethameen C-25.

One interesting feature possessed by Pemulen is that this emulsifying agent is designed to break when the gel is in contact with a salt concentration similar to what one would find on human skin. This is a desirable in the cosmetics industry where moisturizers need to be quickly delivered and absorbed into the user's skin, but this may be a less desirable characteristic of an emulsion designed to clean works of art. In practice, this breakage of the emulsion has been observed when attempting to clean very grimy areas and allowing the gel to dwell for an extended period. Although the vast majority of cream or emulsion products in the marketplace contain water-insoluble actives, the surfactants can re-emulsify the actives and cause wash-off, leaving the skin unprotected.

Those familiar with the art have countered this phenomenon by incorporating waxes or water resistant, film-forming polymers into their formulations. Such a polymer forms an effective barrier, which prevents absorber wash-off, but it may produce negative aesthetic effects such as long rub-in times and a tacky or heavy feel on the skin. However, a novel combination of Ammonium Lactate and Pemulen® polymeric emulsifiers meet the FDA definition of "waterproof" without the use of film-forming polymers, waxes and the like. Because these emulsions contain very little or no surfactants, the water-insoluble UV absorbers remain on the skin, even after an 80 minute exposure to water. The triggered release of the oil phase upon product application ensures that the absorbers are free to spread onto the epidermis where they are immediately active (1). Ammonium lactate is the ammonium salt of lactic acid. This product specially formulates ammonium lactate 20 wt. percent to provide a cream pH of 4.5-6.5. It may also contain glycerin, isopropyl palmitate, dimethicone, ginko biloba, methyl paraben, propyl paraben or butyl parabens fragrance and water.

The percentage of Ammonium lactate is preferably between about 17 to about 20 percent. Optionally, the formulation comprises alpha-Bisabolol, an anti-irritant, and/or a retinoid, such as Tamibarotene, or a triterpenoid such as Betulen [473-98-3] C30H50O2, molecular mass 442.7 and related compounds like betulin, lupeol, and betulinic acid.

Example 6 Ternary Anti-Wrinkle Emulsion of 20 Weight Percent Ammonium Lactate

The formula is a ternary formulation consisting of three parts which are ultimately combined to form a stable oil in water emulsion. The order of addition of the ingredients should be followed strictly as written in Table 4 and the description that follows. Otherwise, the ingredients fall out of solution.

TABLE 4

| Ingredient | Percent | Weight (g) |
|---|---|---|
| Ternary Ingredient-Part 1 Order of Addition | | |
| Demineralized Water | 63.1 | 155.5 |
| Methyl Paraben | 0.1 | 0.5 |
| Propyl Paraben | 0.1 | 0.5 |
| Glycerin | 2.0 | 10.0 |
| Ammonium Lactate (20 wt. %) | 8.0 | 200.0 |
| Total | 73.3 | 366.5 |
| Ternary Ingredient-Part 2 Order of Addition | | |
| Demineralized Water | 18.0 | 90.0 |
| Isopropyl Palmitate | 2.5 | 12.5 |
| Dimethicone (Mw 30,000) | 2.5 | 12.5 |
| White Petrolatum | 1.0 | 5.0 |
| Ginkgo (Ginkgo biloba) | 1.0 | 5.0 |
| Total | 25.0 | 125.0 |
| Ternary Ingredients-Part 3 Order of Addition | | |
| Pemulen ® TR | 1.5 | 7.5 |
| Fragrance (Belle Air #7564) | 0.2 | 1.0 |
| Total | 1.7 | 8.5 |
| Total all 3 parts | 100.0 | 500.0 |

A. Part 1

Part 1 is formed as follows:

a. Add Demineralized water to a 1000 ml beaker. Stirring or Agitation at 600 rpm
b. Add methyl paraben
c. Add propyl paraben
d. Add glycerin
e. Add ammonium Lactate
f. Increase stirring rate or agitation to 1500 rpm B. Part 2

Part 2 is formed as follows:

i. Add demineralized water to an 800 ml beaker. Stir or Agitation at 600 rpm
ii. Add Isopropyl palmitate
iii. Add dimethicone
iv. Add white petrolatum
v. Add gingko biloba
vi. Increase agitation or stirring 1500 rpm
  Mix part 1 and part 2 for 30 minutes
a. Slow agitation or stirring down on part 1 to 600 rpm and blend part 2 into part 1
b. Increase agitation of the combined formulation to 1,800 rpm for 30 minutes c. Part 3

The final formulation is produced as follows:
a. Slow agitation of combined formulation to 600 rpm
b. Add Pemulen® TR1 OR TR2 very slowly (all of it)
c. Increase stirring speed to 1,800 rpm for 30 minutes to disperse all of Pemulen® TR1 OR TR2
d. Increase agitation to 2,800 rpm and hold until the emulsion is smooth and creamy without any of the oils floating on the surface
e. Slow agitation down to 600 rpm and add the fragrance
f. Mix well and place in a proper container (jar or tubes)

Example 7: Ternary Anti-Wrinkle Emulsion of 20 Weight Percent Tamibarotene in Ammonium Lactate A combination tamibarotene and ammonium lactate anti-wrinkle emulsion can be prepared as shown below.

TABLE 5

| Ingredient | Percent | Weight (g) |
|---|---|---|
| Ternary Ingredient-Part 1 Order of Addition | | |
| 1. Demineralized Water | 63.1 | 155.5 |
| 2. Methyl Paraben | 0.1 | 0.5 |
| 3. Propyl Paraben | 0.1 | 0.5 |
| 4. Glycerin | 1.0 | 10.0 |
| 5. Ammonium Lactate (20 wt. %) | 8.0 | 200.0 |
| 6. Tamibarotene (suspended in Ammonium Lactate | 0.05-1.0 | 1.8-3.51 |
| §Total (adjusted according to Active Conentrations) | 73.3 | 370.0 |
| Ternary Ingredient-Part 2 Order of Addition | | |
| 1. Demineralized Water | 18.0 | 90.0 |
| 2. Isopropyl Palmitate | 2.5 | 12.5 |
| 3. Dimethicone (Mw 30,000) | 2.5 | 12.5 |
| 4. White Petrolatum | 1.0 | 5.0 |
| 5. Ginkgo (*Ginkgo biloba*) | 1.0 | 5.0 |
| Total | 25.0 | 125.0 |
| Ternary Ingredients-Part 3 Order of Addition | | |
| 1. Pemulen ® TR | 1.5 | 7.5 |
| 2. Fragrance (Belle Air #7564) | 0.2 | 1.0 |
| 3. Total | 1.7 | 8.5 |
| Total all 3 parts | 100.0 | 500.0 |

A. Part 1.

The order of addition of the ingredients is listed just the way the formulation is written (through all stages). Otherwise, the ingredients fall out of solution.
a. Add Demineralized water to a 1000 ml beaker. Stirring or Agitation at 600 rpm
b. Add methyl paraben
c. Add propyl paraben
d. Add glycerin
e. Add ammonium Lactate
f. Increase stirring rate or agitation to 1500 rpm B. Part 2
a. Add demineralized water to an 800 ml beaker. Stir or Agitation at 600 rpm
b. Add Isopropyl palmitate
c. Add dimethicone
d. Add white petrolatum
e. Add *gingko biloba*
f. Increase agitation or stirring 1500 rpm C. Mix part 1 and part 2 for 30 minutes.

D. Slow agitation or stirring down on part 1 to 600 rpm and blend part 2 into part 1.

E. Increase agitation of the combined formulation to 1,800 rpm for 30 minutes.

F. Part 3
1. Slow agitation of combined formulation to 600 rpm
2. Add Pemulen® TR1 OR TR2 very slowly (all of it)
3. Increase stirring speed to 1,800 rpm for 30 minutes to disperse all of Pemulen® TR1 OR TR2
4. Increase agitation to 2,800 rpm and hold until the emulsion is smooth and creamy without any of the oils floating on the surface.
5. Slow agitation down to 600 rpm and add the fragrance
6. Mix well and place in a proper container (jar or tubes).

One of skill in the art will appreciate that substitutions and deviations from the above formulation may be permissible without departing from the spirit of the invention as long as the changes to not break the emulsion. In particular the use of tinting agents and perfumes are contemplated.

REFERENCES 1. http://www.drugs.com/ingredient/ammonium-lactate.html {http://pubchem.ncbi.nlm.nih.gov/summary/summary.cgi?cid=10586}
2. http://www.lubrizol.com/PersonalCare/Products/Pemulen/PemulenTR-1.html
3. http://pubchem.ncbi.nlm.nih.gov/summary/summary.cgi?cid=1201551 &loc=ec_rcs
4. Y. Hamada, I. Yamada, M. Uenaka, T. Sakata, U.S. Pat. No. 5,214,202 (1993).

In one aspect of the invention, is a composition for reducing the effects of aging comprising tamibarotene in a cosmetically acceptable carrier. In one embodiment, the effects of aging are selected from increase in skin roughness, loss of skin elasticity, increase in skin transparency, skin fragility, increased frequency of bruising, macroscopic appearance of skin wrinkles and folds, and skin discoloration. In one embodiment, the carrier is at least one polyethylene glycol (PEG) of cosmetically acceptable grade. In one embodiment, the polyethylene glycol is a mixture of PEG 300 and PEG 1,540. In another embodiment, the tamibarotene is dissolved in PEG 300 and added to melted PEG 1,540. In one embodiment, the composition further comprises an anti-irritant. In one embodiment, the anti-irritant is (-)-α-Bisabolol. In another embodiment, the composition comprises an antioxidant. In one embodiment, the anti-oxidant is butylated hydroxytoluene (BHT). In another embodiment, the composition is stable at room temperature.

In another aspect of the invention is a topical formulation of tamibarotene co-formulated with ammonium lactate in an acrylates/C10-30 alkyl acrylate crosspolymer. In one embodiment, the topical formulation is a formulation that is a sterically stabilized oil in water (o/w) emulsion. In another embodiment, the ammonium lactate is present from about 17 to about 20 percent by weight. In another embodiment, the composition further comprises an anti-irritant and/or a retinoid. In one embodiment, the anti-irritant is (-)-α-Bisabolol.

In another aspect of the invention is a ternary formulation of tamibarotene comprising:
a. a first part comprising tamibarotene dissolved in at least one paraben, water, and glycerin;

b. a second part comprising water, an emollient, a siloxane, and petrolatum; and
c. a third part comprising the first and second parts together with an acrylates/C 10-30 alkyl acrylate crosspolymer.

In one embodiment, the ternary formulation comprises an additional cosmetic agent.

In another embodiment, the ternary formulation is a formulation in which:
a. the first part comprises demineralized water, methyl paraben, propyl paraben, glycerin, and tamibarotene;
b. the second part comprises demineralized water, isopropyl palmitate, dimethicone, white petrolatum, *gingko biloba*; and
c. the third part comprises parts one and two together with Pemulen™.

In another aspect of the invention is a method of making a ternary formulation of tamibarotene comprising:
a. forming a first part:
   i. adding demineralized water to a 1000 ml beaker;
   ii. stirring or agitation at 600 rpm;
   iii. adding methyl paraben;
   iv. adding propyl paraben;
   v. adding glycerin;
   vi. adding tamibarotene;
   vii. increasing stirring rate or agitation to 1500 rpm;
b. forming a second part by:
   i. adding demineralized water to an 800 ml beaker;
   ii. stirring or agitating at 600 rpm;
   iii. adding isopropyl palmitate;
   iv. adding dimethicone;
   v. adding white petrolatum;
   vi. adding *gingko biloba;*
   vii. increasing agitation or stirring to 1500;
   viii. mix part 1 and part 2 for 30 minutes;
      1. slow agitation or stirring down on part 1 to 600 rpm and blend part 2 into part 1;
      2. increase agitation of the combined formulation to 1,800 rpm for 30 minutes;
c. forming a third part by:
   i. slow agitation of combined formulation of the second part to 600 rpm;
   ii. adding Pemulen™ TR-1 or TR-2 very slowly;
   iii. increasing stirring speed to 1,800 rpm for 30 minutes to disperse all of Pemulen® TR-1 or TR-2;
   iv. increasing agitation to 2,800 rpm and until the emulsion is smooth and creamy without any of the oils floating on the surface;
   v. slowing agitation down to 600 rpm and adding a fragrance; and
   vi. mixing well and placing in a proper vessel.

In another embodiment is a topical formulation of ammonium lactate in an acrylates/C10-30 alkyl acrylate crosspolymer. In one embodiment, the formulation is an oil in water (o/w) emulsion. In one embodiment of the topical formulation, the ammonium lactate is present from about 17 to about 20 percent by weight. In another embodiment, the topical formulation comprises an anti-irritant, and/or a retinoid. In one embodiment, the anti-irritant is (-)-α-Bisabolol and the retinoid is tamibarotene.

In another embodiment is a method of making a ternary formulation of ammonium lactate comprising:
a. forming a first part by:
   i. adding demineralized water to a 1,000 ml beaker;
   ii. stirring or agitating at 600 rpm;
   iii. adding methyl paraben;
   iv. adding propyl paraben;
   v. adding glycerin;
   vi. adding ammonium lactate;
   vii. increasing stirring rate or agitating to 1500 rpm;
b. forming a second part:
   i. adding demineralized water to an 800 ml beaker;
   ii. stirring or agitating at 600 rpm;
   iii. adding isopropyl palmitate;
   iv. adding dimethicone;
   v. adding white petrolatum;
   vi. adding *gingko biloba;*
   vii. increasing stirring rate or agitating to 1,500 rpm;
   viii. mixing part 1 and part 2 for 30 minutes;
   ix. slowly agitating or stirring down part 1 to 600 rpm and blend part 2 into part 1;
   x. increasing the agitation or the stirring rate of the combined formulation to 1,800 rpm for 30 minutes;
c. forming a third part by:
   i. slow agitation or stirring of combined formulation of the second part to 600 rpm;
   ii. adding Pemulen™® TR-1 or TR-2 very slowly (all of it);
   iii. increasing stirring rate to 1,800 rpm for 30 minutes to disperse all of Pemulen™® TR-1 or TR-2;
   iv. increasing agitation to 2,800 rpm and hold until the emulsion is smooth and creamy without any of the oils floating on the surface;
   v. slowing agitation down to 600 rpm and adding fragrance; and
   vi. mixing well and placing in a proper container (jar or tubes).

I claim:

1. A topical formulation for reducing the effects of aging comprising the following components (a) and (b):
   (a) an effective amount of tamibarotene, at least one paraben, water and glycerin;
   wherein the tamibarotene is dissolved in a polyethylene glycol (PEG) mixture of cosmetically acceptable grade,
   wherein the polyethylene glycol mixture consists of PEG 300 and PEG 1,540, and
   wherein the tamibarotene is dissolved in PEG 300 and added to melted PEG 1,540; and
   (b) water, an emollient, a siloxane, and petrolatum;
   wherein the components (a) and (b) are mixed together and dispersed within an acrylates/C 10-30 alkyl acrylate crosspolymer to form the topical formulation.

2. The formulation of claim 1, wherein the effects of aging are selected from increase in skin roughness, loss of skin elasticity, increase in skin transparency, skin fragility, increased frequency of bruising, macroscopic appearance of skin wrinkles and folds, and skin discoloration.

3. The formulation of claim 1, further comprising an anti-irritant.

4. The formulation of claim 3, wherein the anti-irritant is (-)-α-Bisabolol.

5. The formulation of claim 3, further comprising an antioxidant.

6. The formulation of claim 5, wherein the anti-oxidant is butylated hydroxytoluene (BHT).

7. The formulation of claim 1, wherein the formulation is stable at room temperature.

8. The topical formulation of claim 1, wherein the formulation is a sterically stabilized oil in water (o/w) emulsion.

9. The topical formulation of claim 1, further comprising ammonium lactate in an amount of about 17 to 20 percent by weight.

10. The topical formulation of claim 9, further comprising an anti-irritant and/or a retinoid.

11. The topical formulation of claim 10, wherein the anti-irritant is (-)-α-Bisabolol.

12. The formulation of claim 1, further comprising an additional cosmetic agent.

13. The formulation of claim 1,
wherein component (a) comprises tamibarotene, demineralized water, methyl paraben, propyl paraben, and glycerin; and
wherein component (b) comprises demineralized water, isopropyl palmitate, dimethicone, white petrolatum, and *gingko biloba*.

14. The formulation of claim 1, further comprising *ginko biloba*.

15. The formulation of claim 1, wherein the tamibarotene is present from 0.5-15% by weight.

16. A method of making the formulation of claim 1, comprising:
a. forming component (a) by:
  i. adding demineralized water to a vessel;
  ii. stirring or agitation at 600 rpm;
  iii. adding methyl paraben;
  iv. adding propyl paraben;
  v. adding glycerin;
  vi. adding tamibarotene which has been dissolved in a polyethylene glycol mixture of PEG 300 and PEG 1,540; wherein the tamibarotene is dissolved in PEG 300 and added to melted PEG 1,540;
  vii. increasing stirring rate or agitation to 1,500 rpm;
b. forming component (b) by:
  i. adding demineralized water to a vessel;
  ii. stirring or agitating at 600 rpm;
  iii. adding isopropyl palmitate;
  iv. adding dimethicone;
  v. adding white petrolatum;
  vi. optionally adding *gingko biloba;*
  vii. increasing agitation or stirring to 1,500;
  viii. mix part 1 and part 2 for 30 minutes;
    1. slow agitation or stirring down on part 1 to 600 rpm and blend part 2 into part 1;
    2. increase agitation of the combined formulation to 1,800 rpm for 30 minutes;
c. forming the topical composition by:
  i. combining components (a) and (b) then slow agitation of the combined formulation to 600 rpm;
  ii. adding an acrylates/C10-30 alkyl acrylate crosspolymer very slowly;
  iii. increasing stirring speed to 1,800 rpm for 30 minutes to disperse all of the acrylates/C10-30 alkyl acrylate crosspolymer;
  iv. increasing agitation to 2,800 rpm and until the emulsion is smooth and creamy without any of the oils floating on the surface;
  v. slowing agitation down to 600 rpm and adding a fragrance; and
  vi. mixing well and placing in a proper vessel.

17. The method of claim 16, wherein the tamibarotene is present in the formulation from 0.5-15% by weight.

* * * * *

UNITED STATES PATENT AND TRADEMARK OFFICE
CERTIFICATE OF CORRECTION

PATENT NO. : 11,039,995 B2
APPLICATION NO. : 16/380808
DATED : June 22, 2021
INVENTOR(S) : Manzer J. Durrani It is certified that error appears in the above-identified patent and that said Letters Patent is hereby corrected as shown below:

In the Claims

Column 14, Line 40, Claim 1 "1,540" should read --1540--;

Column 14, Line 42, Claim 1 "1,540" should read --1540--;

Column 15, Line 28, Claim 16 "1,540" should read --1540--;

Column 15, Line 29, Claim 16 "1,540" should read --1540--;

Column 15, Line 30, Claim 16 "1,500" should read --1500--;

Column 16, Line 8, Claim 16 "1,500" should read --1500--;

Column 16, Line 13, Claim 16 "1,800" should read --1800--;

Column 16, Line 19, Claim 16 "1,800" should read --1800--;

Column 16, Line 22, Claim 16 "2,800" should read --2800--.

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*